United States Patent [19]

Ueda et al.

[11] Patent Number: 4,777,256

[45] Date of Patent: * Oct. 11, 1988

[54] 5-HALOPYRIDINE-3-CARBOXAMIDE COMPOUNDS

[75] Inventors: Yoichiro Ueda; Kazuhisa Masamoto; Yukihisa Goto, all of Himeji; Yoshiyuki Hirako, Otake; Hiroshi Yagihara, Himeji; Yasuo Morishima, Himeji; Hirokazu Osabe, Himeji, all of Japan

[73] Assignee: Daicel Chemical Industries Ltd., Osaka, Japan

[*] Notice: The portion of the term of this patent subsequent to Feb. 12, 2005 has been disclaimed.

[21] Appl. No.: 816,380

[22] Filed: Jan. 6, 1986

[30] Foreign Application Priority Data

Jan. 17, 1985 [JP] Japan .................................. 60-7279

[51] Int. Cl.⁴ .................. A01N 43/40; C07D 213/82; C07D 401/06; C07D 405/06
[52] U.S. Cl. ........................ 546/291; 546/261; 546/269; 546/272; 546/275; 546/279; 546/280; 546/283; 546/284; 544/238; 544/284; 544/333; 544/353; 544/405; 71/90; 71/92; 71/94
[58] Field of Search ............... 546/291, 284, 283, 280, 546/275, 279, 261, 272, 269; 544/238, 284, 333, 353, 405; 71/90, 92, 94

[56] References Cited

U.S. PATENT DOCUMENTS 4,115,101  9/1978  Carlson .............................. 546/291

Primary Examiner—M. C. Lee
Assistant Examiner—Dale A. Bjorkman

Attorney, Agent, or Firm—Bryan, Cave, McPheeters & McRoberts

[57] ABSTRACT

Novel 5-halopyridine-3-carboxamide compounds having the general formula (I)

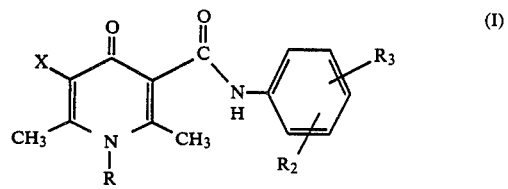

or salts thereof wherein

R is hydrogen atom or a group of —$(CH_2)_n$—$R_1$ wherein n is an integer from 1 to 4 and $R_1$ is hydrogen atom, hydroxy group, lower alkoxy group, mercapto group, lower alkylthio group, amino group, di-lower alkylamino group, $C_{1-11}$ alkyl group, lower alkenyl group, lower alkynyl group, cycloalkyl group, 5- or 6-membered heterocyclic group or aryl group which may be substituted by one or two substituents of halogen, lower alkyl or lower alkoxy;

$R_2$ and $R_3$ are, the same of different, hydrogen atom, halogen atom, cyano group, nitro group, amino group, lower akyl group, halogenated lower alkyl group, hydroxy group, lower alkoxy group, aryloxy group, carboxy group or lower alkoxycarbonyl group;

X is halogen atom; which compounds possess growth inhibitory activities and also anti-inflammatory activity.

10 Claims, No Drawings

5-HALOPYRIDINE-3-CARBOXAMIDE COMPOUNDS

BACKGROUND OF THE INVENTION

1. Field of the Invention

This invention relates to novel compounds which belong to 5-halo-1,4-dihydro-2,6-dimethyl-4-oxo-3-pyridinecarboxamides. The compounds of this invention show growth inhibitory activities on plants and also anti-inflammatory activity.

2. Description of the Prior Arts

Certain compounds belonging to 5-halo-1,4-dihydro-2,6-dimethyl-4-oxo-3-pyridinecarboxamides have been reported in literatures. Canadian Patent No. 1,115,278 [and also J. B. Pierce et al, J. Med. Chem. 25, 131(1982)] disclosed two compounds possessing anti-inflammatory activity, i.e., 5-bromo-1,4-dihydro-2,6-dimethyl-4-oxo-N,1-diphenyl-3-pyridinecarboxamide and 5-bromo-N,1-bis(4-chlorophenyl)-1,4-dihydro-2,6-dimethyl-4-oxo-3-pyridinecarboxamide. When these two compounds are compared with the formula (I) of the present invention, they correspond to the case where R and

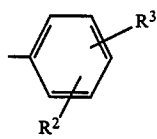

are the same and R is phenyl or a substituted phenyl group.

On the other hand, cephalosporins as pharmaceutical compounds which possess 5-halo-1,4-dihydro-4-oxo-3-pyridinecarboxamides as the partial structure were disclosed in Japanese Patent Unexamined Publication No. Sho 54(1979)-24,892.

However, plant growth inhibitory agents whose active ingredients are 5-halo-1,4-dihydro-2,6-dimethyl-4-oxo-3-pyridinecarboxamides as in the formula (I) shown below are not known.

SUMMARY OF THE INVENTION

This invention is to provide compounds of the formula (I) and salts thereof.

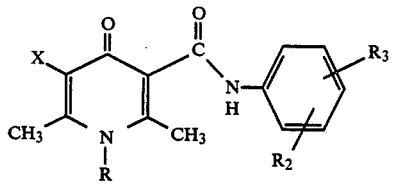

In the formula (I), R is a hydrogen atom or a group of $-(CH_2)_n-R_1$ wherein n is an integer from 1 to 4 and $R_1$ is a hydrogen atom, hydroxy group, lower alkoxy group, mercapto group, lower alkylthio group, amino group, di-lower alkylamino group, $C_{1-11}$ alkyl group, lower alkenyl group, lower alkynyl group, cycloalkyl group, 5- or 6-membered heterocyclic group, or aryl group which may be substituted by one or two substituents of halogen, lower alkyl or lower alkoxy; $R_2$ and $R_3$ are, the same or different, a hydrogen atom, halogen atom, cyano group, nitro group, amino group, lower alkyl group, halogenated lower alkyl group, hydroxy group, lower alkoxy group, aryloxy group, carboxy group or lower alkoxycarbonyl group; x is a halogen atom.

DESCRIPTION OF PREFERRED EMBODIMENTS

The term of "lower" used for lower alkyl, lower alkoxy or like group in this invention means a group containing 1-6 carbon atoms. Specifically, there may be mentioned as lower alkyl groups methyl, ethyl, propyl, isopropyl, butyl, isobutyl, pentyl or isopentyl; as lower alkoxy groups methoxy, ethoxy, propoxy, isopropoxy or butoxy; as lower alkoxycarbonyl groups methoxycarbonyl, ethoxycarbonyl, propoxycarbonyl or butoxycarbonyl; or as lower alkylthio groups methylthio, ethylthio, propylthio, isopropylthio, butylthio or pentylthio. As lower alkenyl or lower alkynyl groups may be mentioned vinyl, allyl, isopropenyl, 2-butenyl, 1,3-butadienyl, 2-pentenyl, 1,4-pentadienyl, 1,6-heptadienyl, 1-hexenyl, ethynyl or 2-propynyl.

Examples of cycloalkyl groups include cyclopropyl, cyclopentyl and cyclohexyl.

5- or 6-membered heterocyclic groups include 5- or 6-membered ones containing one to three hetero atoms selected from nitrogen atom, oxygen atom and sulfur atom. Examples of 5-membered heterocyclic groups are furyl, tetrahydrofuryl, thienyl, thiazolyl, isothiazolyl, oxazolyl, isooxazolyl or pyrazolyl, and examples of 6-membered heterocyclic groups are pyridyl, pyrimidinyl, pyrazinyl or pyridazinyl. These heterocyclic groups may be substituted by alkyl as methyl or ethyl, a halogen atom or phenyl. When the heterocyclic group is substituted by phenyl, it may form a condensed ring combining the two adjacent carbon atoms in the heterocyclic group with the phenyl group. Examples of the condensed ring are a benzothiazolyl, benzofuryl, quinazolinyl or quinoxalinyl group.

Examples of aryl groups include phenyl and naphthyl groups.

Halogen atom includes chlorine, bromine and fluorine atoms.

The compound of the formula (I) in this invention may form an addition salt with an acid such as hydrochloric acid, sulfuric acid, phosphoric acid, methanesulfonic acid, p-toluenesulfonic acid or trifluoroacetic acid when sufficiently basic, and also form a salt with an inorganic base when it contains a carboxylic group. Such salts are also included in this invention.

The compound of the formula (I) in this invention may be prepared by any of the following methods.

Method A

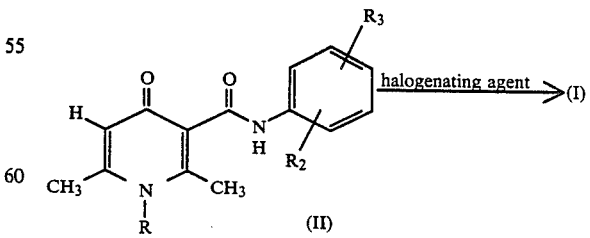

[R, $R_2$ and $R_3$ of the Formula (II) are the same as those in the formula (I)].

This method comprises reacting a 1,4-dihydro-2,6-dimethyl-4-oxo-3-pyridinecarboxamide derivative (II) with a halogenating reagent. It is especially advantageous to use as the halogenating reagent, N-chlorosuccinimide or N-bromosuccinimide in an appropriate chlorinated hydrocarbon solvent (e.g., dichloromethane, chloroform, tetrachloromethane, trichloroethylene or tetrachloroethane) in the presence or absence of a free-radical initiator.

The reaction may be also conducted by dissolving the compound (II) in a halogenated hydrocarbon as mentioned above, and blowing or dropping into the resultant solution bromine or chlorine in gaseous or liquid state.

In the above halogenation of the compound (II), it may additionally give the substitution at the phenyl group which is bonded at the amide nitrogen atom.

Method B

This method is conducted by treating a compound of the formula (I) with an alkali metal halide which concerns an exchange of a halogen atom (X) in the formula (I). It is useful to synthesize a compound of the formula (I) in which X is a fluorine atom and which is difficult to produce by direct introduction.

Method C

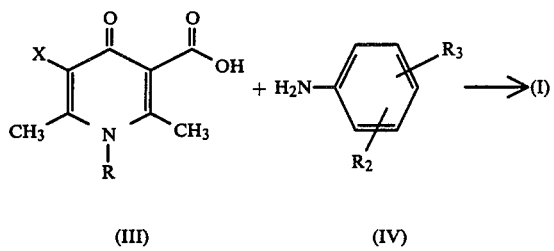

This method is conducted by treating a carboxylic acid of the formula (III) in which R and X are the same as in formula (I) with an aniline derivative (IV) in the presence of an appropriate condensating agent, to yield the compound of the formula(I). As explained in the method A, this method is effective in case where the phenyl group on the amide nitrogen atom is reactive with the halogenating agent.

Method D

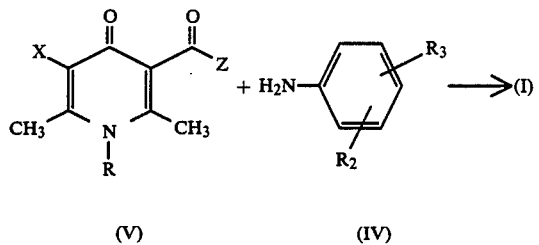

This method is conducted by reacting an acid halide compound of the formula (V) in which R and X are the same as in formula (I) and Z is a chlorine or bromine atom, with an aniline derivative of the formula (IV) in the presence of an appropriate acid removing agent, to obtain a compound of the formula (I). Similarly to the method C, this method is also effective in cases where the phenyl group on the amide nitrogen atom is reactive with the halogenating agent.

Examples of

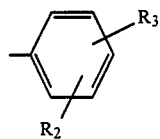

of the formula (I) include phenyl, 2-chlorophenyl, 2-bromophenyl, 2-methylphenyl, 2-ethylphenyl, 2-methoxyphenyl, 3-chlorophenyl, 3-bromophenyl, 3-methylphenyl, 3-ethylphenyl, 3-methoxyphenyl, 4-chlorophenyl, 4-bromophenyl, 4-methylphenyl, 4-ethylphenyl, 4-methoxyphenyl, 2,3-dichlorophenyl, 2,3-dibromophenyl, 2,3-dimethylphenyl, 2,3-diethylphenyl, 2,3-dimethoxyphenyl, 2-methyl-3-chlorophenyl, 2-methyl-3-bromophenyl, 2,4-dichlorophenyl, 2,4-dibromophenyl, 2,4-dimethylphenyl, 2,4-diethylphenyl, 2,4-dimethoxyphenyl, 2-methyl-4-chlorophenyl, 2-methyl-4-bromophenyl, 2,5-dichlorophenyl, 2,5-dibromophenyl, 2,5-dimethylphenyl, 2,5-diethylphenyl, 2,5dimethoxyphenyl, 5-chloro-2-methylphenyl, 5-bromo-2-methylphenyl, 2,6dichlorophenyl, 2,6-dibromophenyl, 2,6-dimethylphenyl, 2,6-diethylphenyl, 2,6-dimethoxyphenyl, 2-chloro-6-methylphenyl, 2-chloro-6-ethylphenyl, 2-bromo-6-methylphenyl, 2-bromo-6-ethylphenyl, 2-methyl-6-ethylphenyl, 2-trifluoromethylphenyl, 3-trifluoromethylphenyl, 4-trifluoromethylphenyl, 2-phenoxyphenyl, 4-phenoxyphenyl, 3-nitrophenyl, 4-nitrophenyl, 4-cyanophenyl, 2-methoxycarbonylphenyl and 4-methoxycarbonylphenyl.

R of the formula (I) includes methyl, ethyl, propyl, butyl, isobutyl, pentyl, isoamyl, hexyl, heptyl, octyl, 2-ethylhexyl, dodecyl, allyl, isopropenyl, 2-butenyl, 3-butenyl, 4-pentenyl, propargyl, 3-butynyl, 2-hydroxyethyl, 3-hydroxypropyl, 2-methoxyethyl, 2-ethoxyethyl, 2-phenoxyethyl, 3-methoxypropyl, 3-ethoxypropyl, 3-isopropoxypropyl, 2-mercaptoethyl, 3-mercaptopropyl, 2-ethylthioethyl, 2-phenylthioethyl, 2-aminoethyl, 2-dimethylaminoethyl, 2-furylmethyl, 2-tetrahydrofurylmethyl, 2-thienylmethyl, 2-pyridylmethyl, 3-pyridyl-methyl, 4-pyridylmethyl, 2-(2-pyridyl)ethyl, phenylmethyl, 2-phenylethyl, 3-phenylpropyl, 4-phenylbutyl, 4-chlorophenylmethyl, 4-fluorophenylmethyl, 4-methylphenylmethyl, 4-isopropylphenylmethyl, 4-trifluoromethylphenylmethyl, 4-methoxyphenylmethyl, 3-methylphenylmethyl, 3-chlorophenylmethyl, 3-methoxyphenylmethyl, 2-(4-methylphenyl)ethyl and 2-(4-chlorophenyl)ethyl.

Furthermore, related specific compounds in addition to the compounds shown in the examples are as follows;
5-bromo-N-(2-chloro-6-methylphenyl)-1,4-dihydro-2,6-dimethyl-4-oxo-1-phenylmethyl-3-pyridinecarboxamide,
5-bromo-N-(4-bromo-2-methoxyphenyl)-1-butyl-1,4-dihydro-2,6-dimethyl-4-oxo-3-pyridinecarboxamide,
5-bromo-N-(4-bromo-2-methoxyphenyl)-1,4-dihydro-2,6-dimethyl-4-oxo-1-(2-phenylethyl)-3-pyridinecarboxamide,
5-chloro-N-(2,6-diethylphenyl)-1,4-dihydro-2,6-dimethyl-4-oxo-3-pyridinecarboxamide,
5-chloro-N-(2,6-diethylphenyl)-1,4-dihydro-1,2,6-trimethyl-4-oxo-3-pyridinecarboxamide,
5-bromo-1-ethyl-N-(2,6-diethylphenyl)-1,4-dihydro-2,6-dimethyl-4-oxo-3-pyridinecarboxamide,
5-chloro-1-ethyl-N-(2,6-diethylphenyl)-1,4-dihydro-2,6-dimethyl-4-oxo-3-pyridinecarboxamide, 5-chloro-N-(2,6-diethylphenyl)-1,4-dihydro-2,6-dimethyl-4-oxo-1-propyl-3-pyridinecarboxamide,
5-bromo-N-(2,6-diethylphenyl)-1,4-dihydro-2,6-dimethyl-1-(2-methylpropyl)-4-oxo-3-pyridinecarboxamide,
5-chloro-N-(2,6-diethylphenyl)-1,4-dihydro-2,6-dimethyl-1-(2-methylpropyl)-4-oxo-3-pyridinecarboxamide,
5-chloro-N-(2,6-diethylphenyl)-1,4-dihydro-2,6-dimethyl-1-(3-methylbutyl)-4-oxo-3-pyridinecarboxamide,
5-chloro-N-(2,6-diethylphenyl)-1-hexyl-1,4-dihydro-2,6-dimethyl-4-oxo-3-pyridinecarboxamide,
1-allyl-5-bromo-N-(2,6-diethylphenyl)-1,4-dihydro-2,6-dimethyl-4-oxo-3-pyridinecarboxamide,
1-allyl-5-chloro-N-(2,6-diethylphenyl)-1,4-dihydro-2,6-dimethyl-4-oxo-3-pyridinecarboxamide,
5-chloro-N-(2,6-diethylphenyl)-1,4-dihydro-2,6-dimethyl-4-oxo-1-propargyl-3-pyridinecarboxamide,
5-bromo-1-cyclohexylmethyl-N-(2,6-diethylphenyl)-1,4-dihydro-2,6-dimethyl-4-oxo-3-pyridinecarboxamide,
5-bromo-N-(2,6-diethylphenyl)-1,4-dihydro-1-(2-methoxyethyl)-2,6-dimethyl-4-oxo-3-pyridinecarboxamide,
5-chloro-N-(2,6-diethylphenyl)-1,4-dihydro-1-(2-methoxyethyl)-2,6-dimethyl-4-oxo-3-pyridinecarboxamide,
5-chloro-N-(2,6-diethylphenyl)-1,4-dihydro-1-(3-methoxypropyl)-2,6-dimethyl-4-oxo-3-pyridinecarboxamide,
5-chloro-1-(2-ethoxymethyl)-N-(2,6-diethylphenyl)-1,4-dihydro-2,6-dimethyl-4-oxo-3-pyridinecarboxamide,
5-bromo-1-(3-ethoxypropyl)-N-(2,6-diethylphenyl)-1,4-dihydro-2,6-dimethyl-4-oxo-3-pyridinecarboxamide,
5-chloro-1-(3-ethoxypropyl)-N-(2,6-diethylphenyl)-1,4-dihydro-2,6-dimethyl-4-oxo-3-pyridinecarboxamide,
5-bromo-N-(2,6-diethylphenyl)-1,4-dihydro-1-(2-isopropoxyethyl)-2,6-dimethyl-4-oxo-3-pyridinecarboxamide,
5-chloro-N-(2,6-diethylphenyl)-1,4-dihydro-1-(2-isopropoxyethyl)-2,6-dimethyl-4-oxo-3-pyridinecarboxamide,
5-bromo-N-(2,6-diethylphenyl)-1,4-dihydro-1-(3-isopropoxypropyl)-2,6-dimethyl-4-oxo-3-pyridinecarboxamide,
5-chloro-N-(2,6-diethylphenyl)-1,4-dihydro-1-(3-isopropoxypropyl)-2,6-dimethyl-4-oxo-3-pyridinecarboxamide,
5-bromo-N-(2,6-diethylphenyl)-1-(2-ethylthioethyl)-1,4-dihydro-2,6-dimethyl-4-oxo-3-pyridinecarboxamide,
5-chloro-N-(2,6-diethylphenyl)-1-(2-ethylthioethyl)-1,4-dihydro-2,6-dimethyl-4-oxo-3-pyridinecarboxamide,
5-chloro-N-(2,6-diethylphenyl)-1,4-dihydro-2,6-dimethyl-4-oxo-1-phenylmethyl-3-pyridinecarboxamide,
5-bromo-1-(3-chlorophenylmethyl)-N-(2,6-diethylphenyl)-1,4-dihydro-2,6-dimethyl-4-oxo-3-pyridinecarboxamide,
5-chloro-1-(3-chlorophenylmethyl)-N-(2,6-diethylphenyl)-1,4-dihydro-2,6-dimethyl-4-oxo-3-pyridinecarboxamide,
5-bromo-1-(4-chlorophenylmethyl)-N-(2,6-diethylphenyl)-1,4-dihydro-2,6-dimethyl-4-oxo-3-pyridinecarboxamide,
5-chloro-1-(4-chlorophenylmethyl)-N-(2,6-diethylphenyl)-1,4-dihydro-2,6-dimethyl-4-oxo-3-pyridinecarboxamide,
5-bromo-N-(2,6-diethylphenyl)-1,4-dihydro-2,6-dimethyl-4-oxo-1-(3-methylphenylmethyl)-3-pyridinecarboxamide,
5-chloro-N-(2,6-diethylphenyl)-1,4-dihydro-2,6-dimethyl-4-oxo-1-(3-methylphenylmethyl)-3-pyridinecarboxamide,
5-bromo-N-(2,6-diethylphenyl)-1,4-dihydro-2,6-dimethyl-4-oxo-1-(4-methylphenylmethyl)-3-pyridinecarboxamide,
5-chloro-N-(2,6-diethylphenyl)-1,4-dihydro-2,6-dimethyl-4-oxo-1-(4-methylphenylmethyl)-3-pyridinecarboxamide,
5-chloro-N-(2,6-diethylphenyl)-1,4-dihydro-2,6-dimethyl-4-oxo-1-(2-phenylethyl)-3-pyridinecarboxamide,
5-bromo-N-(2,6-diethylphenyl)-1,4-dihydro-2,6-dimethyl-4-oxo-1-(3-phenylpropyl)-3-pyridinecarboxamide,
5-chloro-N-(2,6-diethylphenyl)-1,4-dihydro-2,6-dimethyl-4-oxo-1-(3-phenylpropyl)-3-pyridinecarboxamide,
5-bromo-N-(2,6-diethylphenyl)-1,4-dihydro-2,6-dimethyl-4-oxo-1-(4-phenylbutyl)-3-pyridinecarboxamide,
5-chloro-N-(2,6-diethylphenyl)-1,4-dihydro-2,6-dimethyl-4-oxo-1-(4-phenylbutyl)-3-pyridinecarboxamide,
5-chloro-N-(2,6-diethylphenyl)-1-(2-furyl)-1,4-dihydro-2,6-dimethyl-4-oxo-3-pyridinecarboxamide,
5-bromo-1,4-dihydro-1,2,6-trimethyl-N-(2,6-dimethylphenyl)-4-oxo-3-pyridinecarboxamide,
5-bromo-1-butyl-1,4-dihydro-1-propargyl-N-(2,6-dimethylphenyl)-4-oxo-3-pyridinecarboxamide,
5-chloro-1,4-dihydro-2,6-dimethyl-N-(2,6-dimethylphenyl)-4-oxo-1-pentyl-3-pyridinecarboxamide,
5-chloro-1,4-dihydro-1-hexyl-2,6-dimethyl-N-(2,6-dimethylphenyl)-4-oxo-3-pyridinecarboxamide,
5-bromo-1,4-dihydro-1-(2-methoxyethyl)-2,6-dimethyl-N-(2,6-dimethylphenyl)-4-oxo-3-pyridinecarboxamide,
5-bromo-1,4-dihydro-1-(3-methoxypropyl)-2,6-dimethyl-N-(2,6-dimethylphenyl)-4-oxo-3-pyridinecarboxamide,
5-bromo-1-(2-ethoxyethyl)-1,4-dihydro-2,6-dimethyl-N-(2,6-dimethylphenyl)-4-oxo-3-pyridinecarboxamide,
5-bromo-1-(3-ethoxypropyl)-1,4-dihydro-2,6-dimethyl-N-(2,6-dimethylphenyl)-4-oxo-3-pyridinecarboxamide,
5-bromo-1-(2-ethylthioethyl)-1,4-dihydro-2,6-dimethyl-N-(2,6-dimethylphenyl)-4-oxo-3-pyridinecarboxamide,
5-bromo-N-(2-ethyl-6-methylphenyl)-1,4-dihydro-2,6-dimethyl-4-oxo-3-pyridinecarboxamide,
5-bromo-N-(2-ethyl-6-methylphenyl)-1,4-dihydro-1,2,6-trimethyl-4-oxo-3-pyridinecarboxamide,
5-bromo-1-ethyl-N-(2-ethyl-6-methylphenyl)-1,4-dihydro-2,6-dimethyl-4-oxo-3-pyridinecarboxamide,
5-bromo-N-(2-ethyl-6-methylphenyl)-1,4-dihydro-2,6-dimethyl-4-oxo-1-propyl-3-pyridinecarboxamide,
1-butyl-5-chloro-N-(2-ethyl-6-methylphenyl)-1,4-dihydro-2,6-dimethyl-4-oxo-3-pyridinecarboxamide,
5-bromo-N-(2-ethyl-6-methylphenyl)-1,4-dihydro-2,6-dimethyl-1-(2-methylpropyl)-4-oxo-3-pyridinecarboxamide,
5-chloro-N-(2-ethyl-6-methylphenyl)-1,4-dihydro-2,6-dimethyl-1-(2-methylpropyl)-4-oxo-3-pyridinecarboxamide,
5-bromo-N-(2-ethyl-6-methylphenyl)-1,4-dihydro-2,6-dimethyl-4-oxo-1-pentyl-3-pyridinecarboxamide,
5-chloro-N-(2-ethyl-6-methylphenyl)-1,4-dihydro-2,6-dimethyl-4-oxo-1-pentyl-3-pyridinecarboxamide, 5-bromo-N-(2-ethyl-6-methylphenyl)-1,4-dihydro-2,6-dimethyl-1-(3-methylbutyl)-4-oxo-3-pyridinecarboxamide,
5-chloro-N-(2-ethyl-6-methylphenyl)-1,4-dihydro-2,6-dimethyl-1-(3-methylbutyl)-4-oxo-3-pyridinecarboxamide,
5-bromo-N-(2-ethyl-6-methylphenyl)-1-hexyl-1,4-dihydro-2,6-dimethyl-4-oxo-3-pyridinecarboxamide,
5-chloro-N-(2-ethyl-6-methylphenyl)-1-hexyl-1,4-dihydro-2,6-dimethyl-4-oxo-3-pyridinecarboxamide,
1-allyl-5-bromo-N-(2-ethyl-6-methylphenyl)-1,4-dihydro-2,6-dimethyl-4-oxo-3-pyridinecarboxamide,
5-bromo-N-(2-ethyl-6-methylphenyl)-1,4-dihydro-2,6-dimethyl-4-oxo-1-propargyl-3-pyridinecarboxamide,
5-bromo-N-(2-ethyl-6-methylphenyl)-1,4-dihydro-1-(2-methoxyethyl)-2,6-dimethyl-4-oxo-3-pyridinecarboxamide,
5-bromo-N-(2-ethyl-6-methylphenyl)-1,4-dihydro-1-(3-methoxypropyl)-2,6-dimethyl-4-oxo-3-pyridinecarboxamide,
5-bromo-1-(2-ethoxyethyl)-N-(2-ethyl-6-methylphenyl)-1,4-dihydro-2,6-dimethyl-4-oxo-3-pyridinecarboxamide,
5-bromo-1-(3-ethoxypropyl)-N-(2-ethyl-6-methylphenyl)-1,4-dihydro-2,6-dimethyl-4-oxo-3-pyridinecarboxamide,
5-bromo-N-(2-ethyl-6-methylphenyl)-1-(2-ethylthioethyl)-1,4-dihydro-2,6-dimethyl-4-oxo-3-pyridinecarboxamide,
5-chloro-1,4-dihydro-2,6-dimethyl-N-(2,6-dimethylphenyl)-4-oxo-1-phenylmethyl-3-pyridinecarboxamide,
5-bromo-1-(3-chlorophenylmethyl)-1,4-dihydro-2,6-dimethyl-N-(2,6-dimethylphenyl)-4-oxo-3-pyridinecarboxamide,
5-bromo-1-(4-chlorophenylmethyl)-1,4-dihydro-2,6-dimethyl-N-(2,6-dimethylphenyl)-4-oxo-3-pyridinecarboxamide,
5-bromo-1,4-dihydro-2,6-dimethyl-N-(2,6-dimethylphenyl)-1-(3-methylphenylmethyl)-4-oxo-3-pyridinecarboxamide,
5-bromo-1,4-dihydro-2,6-dimethyl-N-(2,6-dimethylphenyl)-1-(4-methylphenylmethyl)-4-oxo-3-pyridinecarboxamide,
5-chloro-1,4-dihydro-2,6-dimethyl-N-(2,6-dimethylphenyl)-4-oxo-1-(2-phenylethyl)-3-pyridinecarboxamide,
5-bromo-1,4-dihydro-2,6-dimethyl-N-(2,6-dimethylphenyl)-4-oxo-1-(3-phenylpropyl)-3-pyridinecarboxamide,
5-bromo-1,4-dihydro-2,6-dimethyl-N-(2,6-dimethylphenyl)-4-oxo-1-(4-phenylbutyl)-3-pyridinecarboxamide,
5-bromo-N-(2-ethyl-6-methylphenyl)-1,4-dihydro-2,6-dimethyl-4-oxo-1-phenylmethyl-3-pyridinecarboxamide,
5-chloro-N-(2-ethyl-6-methylphenyl)-1,4-dihydro-2,6-dimethyl-4-oxo-1-phenylmethyl-3-pyridinecarboxamide,
5-bromo-1-(3-chlorophenylmethyl)-N-(2-ethyl-6-methylphenyl)-1,4-dihydro-2,6-dimethyl-4-oxo-3-pyridinecarboxamide,
5-bromo-1-(4-chlorophenylmethyl)-N-(2-ethyl-6-methylphenyl)-1,4-dihydro-2,6-dimethyl-4-oxo-3-pyridinecarboxamide,
5-chloro-1-(4-chlorophenylmethyl)-N-(2-ethyl-6-methylphenyl)-1,4-dihydro-2,6-dimethyl-4-oxo-3-pyridinecarboxamide,
5-bromo-N-(2-ethyl-6-methylphenyl)-1,4-dihydro-2,6-dimethyl-1-(3-methylphenyl)-4-oxo-3-pyridinecarboxamide,
5-bromo-N-(2-ethyl-6-methylphenyl)-1,4-dihydro-2,6-dimethyl-1-(4-methylphenylmethyl)-4-oxo-3-pyridinecarboxamide,
5-chloro-N-(2-ethyl-6-methylphenyl)-1,4-dihydro-2,6-dimethyl-1-(4-methylphenylmethyl)-4-oxo-3-pyridinecarboxamide,
5-chloro-N-(2-ethyl-6-methylphenyl)-1,4-dihydro-2,6-dimethyl-4-oxo-1-(2-phenylethyl)-3-pyridinecarboxamide,
5-bromo-N-(2-ethyl-6-methylphenyl)-1,4-dihydro-2,6-dimethyl-4-oxo-1-(3-phenylpropyl)-3-pyridinecarboxamide,
5-bromo-N-(2-ethyl-6-methylphenyl)-1,4-dihydro-2,6-dimethyl-4-oxo-1-(4-phenylbutyl)-3-pyridinecarboxamide,
5-bromo-1-butyl-1,4-dihydro-N-(2,6-diisopropylphenyl)-2,6-dimethyl-4-oxo-3-pyridinecarboxamide,
5-chloro-1-butyl-1,4-dihydro-N-(2,6-diisopropylphenyl)-2,6-dimethyl-4-oxo-3-pyridinecarboxamide,
5-bromo-1,4-dihydro-N-(2,6-diisopropylphenyl)-2,6-dimethyl-1-(2-methylpropyl)-4-oxo-3-pyridinecarboxamide,
5-chloro-1,4-dihydro-N-(2,6-diisopropylphenyl)-2,6-dimethyl-1-(2-methylpropyl)-4-oxo-3-pyridinecarboxamide,
5-bromo-1,4-dihydro-N-(2,6-diisopropylphenyl)-2,6-dimethyl-4-oxo-1-pentyl-3-pyridinecarboxamide,
5-chloro-1,4-dihydro-N-(2,6-diisopropylphenyl)-2,6-dimethyl-4-oxo-1-pentyl-3-pyridinecarboxamide,
5-bromo-1,4-dihydro-N-(2,6-diisopropylphenyl)-2,6-dimethyl-1-(3-methylbutyl)-4-oxo-3-pyridinecarboxamide,
5-chloro-1,4-dihydro-N-(2,6-diisopropylphenyl)-2,6-dimethyl-1-(3-methylbutyl)-4-oxo-3-pyridinecarboxamide,
5-bromo-1-hexyl-1,4-dihydro-N-(2,6-diisopropylphenyl)-2,6-dimethyl-4-oxo-3-pyridinecarboxamide,
5-chloro-1-hexyl-1,4-dihydro-N-(2,6-diisopropylphenyl)-2,6-dimethyl-4-oxo-3-pyridinecarboxamide,
5-bromo-1,4-dihydro-N-(2,6-diisopropylphenyl)-1-(2-methoxyethyl)-2,6-dimethyl-4-oxo-3-pyridinecarboxamide,
5-chloro-1,4-dihydro-N-(2,6-diisopropylphenyl)-1-(2-methoxyethyl)-2,6-dimethyl-4-oxo-3-pyridinecarboxamide,
5-bromo-1,4-dihydro-N-(2,6-diisopropylphenyl)-1-(3-methoxypropyl)-2,6-dimethyl-4-oxo-3-pyridinecarboxamide,
5-chloro-1,4-dihydro-N-(2,6-diisopropylphenyl)-1-(3-methoxypropyl)-2,6-dimethyl-4-oxo-3-pyridinecarboxamide,
5-bromo-1-(2-ethoxyethyl)-1,4-dihydro-N-(2,6-diisopropylphenyl)-2,6-dimethyl-4-oxo-3-pyridinecarboxamide,
5-chloro-1-(2-ethoxyethyl)-1,4-dihydro-N-(2,6-diisopropylphenyl)-2,6-dimethyl-4-oxo-3-pyridinecarboxamide,
5-bromo-1-(3-ethoxypropyl)-1,4-dihydro-N-(2,6-diisopropylphenyl-2,6-dimethyl-4-oxo-3-pyridinecarboxamide,
5-chloro-1-(3-ethoxypropyl)-1,4-dihydro-N-(2,6-diisopropylphenyl)-2,6-dimethyl-4-oxo-3-pyridinecarboxamide, 5-bromo-1,4-dihydro-1-(2-isopropoxyethyl)-N-(2,6-diisopropylphenyl)-2,6-dimethyl-4-oxo-3-pyridinecarboxamide,
5-chloro-1,4-dihydro-1-(2-isopropoxyethyl)-N-(2,6-diisopropylphenyl)-2,6-dimethyl-4-oxo-3-pyridinecarboxamide,
5-bromo-1,4-dihydro-1-(3-isopropoxypropyl)-N-(2,6-diisopropylphenyl)-2,6-dimethyl-4-oxo-3-pyridinecarboxamide,
5-chloro-1,4-dihydro-1-(3-isopropoxypropyl)-N-(2,6-diisopropylphenyl)-2,6-dimethyl-4-oxo-3-pyridinecarboxamide,
5-bromo-1,4-dihydro-N-(2,6-diisopropylphenyl)-2,6-dimethyl-4-oxo-1-phenylmethyl-3-pyridinecarboxamide,
5-chloro-1,4-dihydro-N-(2,6-diisopropylphenyl)-2,6-dimethyl-4-oxo-1-phenylmethyl-3-pyridinecarboxamide,
5-bromo-1-(3-chlorophenylmethyl)1,4-dihydro-N-(2,6-diisopropylphenyl)-2,6-dimethyl-4-oxo-3-pyridinecarboxamide,
5-bromo-1-(4-chlorophenylmethyl)-1,4-dihydro-N-(2,6-diisopropylphenyl)-2,6-dimethyl-4-oxo-3-pyridinecarboxamide,
5-chloro-1-(4-chlorophenylmethyl)-1,4-dihydro-N-(2,6-diisopropylphenyl)-2,6-dimethyl-4-oxo-3-pyridinecarboxamide,
5-bromo-1,4-dihydro-N-(2,6-diisopropylphenyl)-2,6-dimethyl-1-(3-methylphenylmethyl)-4-oxo-3-pyridinecarboxamide,
5-bromo-1,4-dihydro-N-(2,6-diisopropylphenyl)-2,6-dimethyl-1-(4-methylphenylmethyl)-4-oxo-3-pyridinecarboxamide,
5-chloro-1,4-dihydro-N-(2,6-diisopropylphenyl)-2,6-dimethyl-1-(4-methylphenylmethyl)-4-oxo-3-pyridinecarboxamide,
5-bromo-1,4-dihydro-N-(2,6-diisopropylphenyl)-2,6-dimethyl-4-oxo-1-(2-phenylethyl)-3-pyridinecarboxamide,
5-chloro-1,4-dihydro-N-(2,6-diisopropylphenyl)-2,6-dimethyl-4-oxo-1-(2-phenylethyl)-3-pyridinecarboxamide,
5-bromo-1,4-dihydro-N-(2,6-diisopropylphenyl)-2,6-dimethyl-4-oxo-1-(3-phenylpropyl)-3-pyridinecarboxamide,
5-bromo-1,4-dihydro-N-(2,6-diisopropylphenyl)-2,6-dimethyl-4-oxo-1-(4-phenylbutyl)-3-pyridinecarboxamide,
N-(2,6-diethylphenyl)-5-fluoro-1,4-dihydro-2,6-dimethyl-4-oxo-1-propyl-3-pyridinecarboxamide,
1-butyl-N-(2,6-diethylphenyl)-5-fluoro-1,4-dihydro-2,6-dimethyl-4-oxo-3-pyridinecarboxamide,
N-(2,6-diethylphenyl)-5-fluoro-1,4-dihydro-2,6-dimethyl-1-(2-methylpropyl)-4-oxo-3-pyridinecarboxamide,
N-(2,6-diethylphenyl)-5-fluoro-1,4-dihydro-2,6-dimethyl-4-oxo-1-pentyl-3-pyridinecarboxamide,
N-(2,6-diethylphenyl)-5-fluoro-1,4-dihydro-2,6-dimethyl-1-(3-methylbutyl)-4-oxo-3-pyridinecarboxamide,
N-(2,6-diethylphenyl)-5-fluoro-1-hexyl-1,4-dihydro-2,6-dimethyl-4-oxo-3-pyridinecarboxamide,
N-(2,6-diethylphenyl)-5-fluoro-1,4-dihydro-1-(2-methoxyethyl)-2,6-dimethyl-4-oxo-3-pyridinecarboxamide,
N-(2,6-diethylphenyl)-5-fluoro-1,4-dihydro-1-(3-methoxypropyl)-2,6-dimethyl-4-oxo-3-pyridinecarboxamide,
1-(2-ethoxyethyl)-N-(2,6-diethylphenyl)-5-fluoro-1,4-dihydro-2,6-dimethyl-4-oxo-3-pyridinecarboxamide,
1-(3-ethoxypropyl)-N-(2,6-diethylphenyl)-5-fluoro-1,4-dihydro-2,6-dimethyl-4-oxo-3-pyridinecarboxamide,
N-(2,6-diethylphenyl)-5-fluoro-1,4-dihydro-1-(2-isopropoxyethyl)-2,6-dimethyl-4-oxo-3-pyridinecarboxamide,
N-(2,6-diethylphenyl)-5-fluoro-1,4-dihydro-1-(3-isopropoxypropyl)-2,6-dimethyl-4-oxo-3-pyridinecarboxamide,
N-(2,6-diethylphenyl)-5-fluoro-1,4-dihydro-2,6-dimethyl-4-oxo-1-phenylmethyl-3-pyridinecarboxamide,
1-(3-chlorophenylmethyl)-N-(2,6-diethylphenyl)-5-fluoro-1,4-dihydro-2,6-dimethyl-4-oxo-3-pyridinecarboxamide,
1-(4-chlorophenylmethyl)-N-(2,6-diethylphenyl)-5-fluoro-1,4-dihydro-2,6-dimethyl-4-oxo-3-pyridinecarboxamide,
N-(2,6-diethylphenyl)-5-fluoro-1,4-dihydro-2,6-dimethyl-1-(3-methylphenylmethyl)-4-oxo-3-pyridinecarboxamide,
N-(2,6-diethylphenyl)-5-fluoro-1,4-dihydro-2,6-dimethyl-1-(4-methylphenylmethyl)-4-oxo-3-pyridinecarboxamide,
N-(2,6-diethylphenyl)-5-fluoro-1,4-dihydro-2,6-dimethyl-4-oxo-1-(2-phenylethyl)-3-pyridinecarboxamide,
N-(2,6-diethylphenyl)-5-fluoro-1,4-dihydro-2,6-dimethyl-4-oxo-1-(3-phenylpropyl)-3-pyridinecarboxamide,
N-(2,6-diethylphenyl)-5-fluoro-1,4-dihydro-2,6-dimethyl-4-oxo-1-(4-phenylbutyl)-3-pyridinecarboxamide,
1-butyl-5-fluoro-1,4-dihydro-2,6-dimethyl-N-(2,6-dimethylphenyl)-4-oxo-3-pyridinecarboxamide,
5-fluoro-1-hexyl-1,4-dihydro-2,6-dimethyl-N-(2,6-dimethylphenyl)-4-oxo-3-pyridinecarboxamide,
5-fluoro-1,4-dihydro-1-(2-methoxyethyl)-2,6-dimethyl-N-(2,6-dimethylphenyl)-4-oxo-3-pyridinecarboxamide,
5-fluoro-1,4-dihydro-1-(3-methoxypropyl)-2,6-dimethyl-N-(2,6-dimethylphenyl)-4-oxo-3-pyridinecarboxamide.
5-fluoro-1,4-dihydro-2,6-dimethyl-N-(2,6-dimethylphenyl)-4-oxo-1-phenylmethyl-3-pyridinecarboxamide,
1-(4-chlorophenylmethyl)-5-fluoro-1,4-dihydro-2,6-dimethyl-N-(2,6-diemethylphenyl)-4-oxo-3-pyridinecarboxamide,
5-fluoro-1,4-dihydro-2,6-dimethyl-N-(2,6-dimethylphenyl)-1-(4-methylphenylmethyl)-4-oxo-3-pyridinecarboxamide,
5-fluoro-1,4-dihydro-2,6-dimethyl-N-(2,6-dimethylphenyl)-4-oxo-1-(2-phenylethyl)-3-pyridinecarboxamide,
1-butyl-N-(2-ethyl-6-methylphenyl)-5-fluoro-1,4-dihydro-2,6-dimethyl-4-oxo-3-pyridinecarboxamide,
N-(2-ethyl-6-methylphenyl)-5-fluoro-1-hexyl-1,4-dihydro-2,6-dimethyl-4-oxo-3-pyridinecarboxamide,
N-(2-ethyl-6-methylphenyl)-5-fluoro-1,4-dihydro-1-(2-methoxyethyl)-2,6-dimethyl-4-oxo-3-pyridinecarboxamide,
N-(2-ethyl-6-methylphenyl)-5-fluoro-1,4-dihydro-1-(3-methoxypropyl)-2,6-dimethyl-4-oxo-3-pyridinecarboxamide,
N-(2-ethyl-6-methylphenyl)-5-fluoro-1,4-dihydro-2,6-dimethyl-4-oxo-1-phenylmethyl-3-pyridinecarboxamide,
1-(4-chlorophenylmethyl)-N-(2-ethyl-6-methylphenyl)-5-fluoro-1,4-dihydro-2,6-dimethyl-4-oxo-3-pyridinecarboxamide, N-(2-ethyl-6-methylphenyl)-5-fluoro-1,4-dihydro-2,6-dimethyl-1-(4-methylphenylmethyl)-4-oxo-3-pyridinecarboxamide, N-(2-ethyl-6-methylphenyl)-5-fluoro-1,4-dihydro-2,6-dimethyl-4-oxo-1-(2-phenylethyl)-3-pyridinecarboxamide, 1-butyl-5-fluoro-1,4-dihydro-N-(2,6-diisopropylphenyl)-2,6-dimethyl-4-oxo-3-pyridinecarboxamide, 5-fluoro-1-hexyl-1,4-dihydro-N-(2,6-diisopropylphenyl)-2,6-dimethyl-4-oxo-3-pyridinecarboxamide, 5-fluoro-1,4-dihydro-N-(2,6-diisopropylphenyl)-1-(2-methoxyethyl)-2,6-dimethyl-4-oxo-3-pyridinecarboxamide, 5-fluoro-1,4-dihydro-N-(2,6-diisopropylphenyl)-1-(3-methoxypropyl)-2,6-dimethyl-4-oxo-3-pyridinecarboxamide, 5-fluoro-1,4-dihydro-N-(2,6-diisopropylphenyl)-2,6-dimethyl-4-oxo-1-phenylmethyl-3-pyridinecarboxamide, 1-(4-chlorophenylmethyl)-5-fluoro-1,4-dihydro-N-(2,6-diisopropylphenyl)-2,6-dimethyl-4-oxo-3-pyridinecarboxamide, 5-fluoro-1,4-dihydro-N-(2,6-diisopropylphenyl)-2,6-dimethyl-1-(4-methylphenylmethyl)-4-oxo-3-pyridinecarboxamide, 5-fluoro-1,4-dihydro-N-(2,6-diisopropylphenyl)-2,6-dimethyl-4-oxo-1-(2-phenylethyl)-3-pyridinecarboxamide, 1-(2-ethoxyethyl)-N-(2-ethyl-6-methylphenyl)-5-fluoro-1,4-dihydro-2,6-dimethyl-4-oxo-3-pyridinecarboxamide, 1-(3-ethoxypropyl)-N-(2-ethyl-6-methylphenyl)-5-fluoro-1,4-dihydro-2,6-dimethyl-4-oxo-3-pyridinecarboxamide.

This invention is further illustrated by examples hereinafter. Also, growth-inhibitory activities on plants of the compounds of the invention are shown in reference examples.

EXAMPLE 1

5-Bromo-1-butyl-N-(2,6-diethylphenyl)-1,4-dihydro-2,6-dimethyl-4-oxo-3-pyridinecarboxamide (compound 1)

A mixture of 3.0 g (8.5 mmol, m.p. 110°–112° C.) of 1-butyl-N-(2,6-diethylphenyl)-1,4-dihydro-2,6-dimethyl-4-oxo-3-pyridinecarboxamide and 1.7 g (9.6 mmol) of N-bromosuccinimide was dissolved in 100 ml of dichloromethane, and the mixture was stirred for a day at room temperature. The reaction mixture, transferred to a separatory funnel, was washed with water, saturated sodium bicarbonate and water. The organic layer was dried and concentrated in a known manner to give a crystalline residue, and the residue was recrystallized from a mixture of ethyl acetate and hexane, affording 2.25 g of the title compound having m.p. 158°–160.5° C.

EXAMPLE 2

1-Butyl-5-chloro-N-(2,6-diethylphenyl)-1,4-dihydro-2,6-dimethyl-4-oxo-3-pyridinecarboxamide (compound 2)

A mixture of 500 mg (1.41 mmol, m.p. 110°–112° C.) of 1-butyl-N-(2,6-diethylphenyl)-1,4-dihydro-2,6-dimethyl-4-oxo-3-pyridinecarboxamide and 188 mg (1.41 mmol) of N-chlorosuccinimide was dissolved in 15 ml of chloroform and refluxed with stirring. To the reaction mixture, 190 mg of N-chloro-succinimide was added in twice, and refluxed for 15.2 hours.

The reaction mixture, transferred to a separatory funnel, was washed with water, saturated sodium bicarbonate and water. The organic layer was dried and concentrated in a usual manner to give a yellow oil, which was purified by column chromatography (Wacogel ® C-200) with a mixture of ethyl acetate and hexane. A crystalline residue was recrystallized from a mixture of ethyl acetate and hexane, affording 300 mg of title compound having m.p. 125.5°–126.5° C.

EXAMPLE 3

5-Bromo-N-(4-bromo-2-methylphenyl)-1-butyl-1,4-dihydro-2,6-dimethyl-4-oxo-3-pyridinecarboxamide (compound 3)

A mixture of 1.00 g (3.20 mmol, m.p. 143°–145° C.) of 1-butyl-1,4-dihydro-2,6-dimethyl-N-(2-methylphenyl)4-oxo-3-pyridinecarboxamide and 0.63 g (3.52 mmol) of N-bromosuccinimide was dissolved in 30 ml of dichloromethane, and the mixture was stirred for two days at room temperature, then 0.63 g of N-bromosuccinimide was added, and stirred for four days. The reaction mixture, transferred to a separatory funnel, was washed water, saturated sodium bicarbonate and water. The organic layer was dried and concentrated in a usual manner to give a crystalline residue. The residue was recrystallized from a mixture of ethyl acetate and methanol, affording 1.04 g (yield: 71%) of the title compound having m.p. 190°–192.5° C.

The following Table 1 and Table 2 show physical properties of the compounds associated with this invention. Numbers in the columns "Evaluation" in Table 2 were obtained as follows.

A carrier was prepared by mixing 50 parts (by weight) of talc, 25 parts of bentonite, 2 parts of Solpole-9047 (Toho Chemical Co., Ltd., Japan) and 3 parts of Solpole-5039 (Toho Chemical Co., Ltd., Japan). 50 parts of a test compound and 200 parts of the carrier were mixed to obtain 20% wettable powder, followed by dispersing the powder in distilled water to make dispersions of the definite concentrations.

Seeds of Oryza sativa L., Echinochloa crus-galli L., and Raphanus sativus L. were germinated in a laboratory dish, to which the dispersion was added. After breeding for 7 days in a thermostatic box kept at 25° C. under illumination of fluorescent tubes, growth of plant was observed. In the column of "Evaluation" of Table 2, the designation 1 denotes no influence, 2 denotes 25% growth inhibition, 3 denotes 50% growth inhibition, 4 denotes 75% growth inhibition and 5 denotes 100% growth inhibition.

TABLE 1

| Example No. | R | $R_2$ | $R_3$ | X | Melting Point (°C.) | Molecular Formula |
|---|---|---|---|---|---|---|
| 1 | butyl | 2-$C_2H_5$ | 6-$C_2H_5$ | Br | 158–160.5 | $C_{22}H_{29}BrN_2O_2$ |
| 2 | butyl | 2-$C_2H_5$ | 6-$C_2H_5$ | Cl | 125.5–126.5 | $C_{22}H_{29}ClN_2O_2$ |

TABLE 1-continued

| Example No. | R | $R_2$ | $R_3$ | X | Melting Point (°C.) | Molecular Formula |
|---|---|---|---|---|---|---|
| 3 | butyl | 2-$CH_3$ | 4-Br | Br | 190-192.5 | $C_{19}H_{22}Br_2N_2O_2$ |
| 4 | butyl | 2-Cl | H | Br | 165-166.5 | $C_{18}H_{20}BrClN_2O_2$ |
| 5 | phenylmethyl | 2-Cl | H | Br | 202-206 | $C_{21}H_{18}BrClN_2O_2$ |
| 6 | 2-phenylethyl | 2-Cl | H | Br | 187.5-192 | $C_{22}H_{20}BrClN_2O_2$ |
| 7 | butyl | 2-$CH_3$ | 6-$CH_3$ | Br | 151-153 | $C_{20}H_{25}BrN_2O_2$ |
| 8 | pentyl | 2-$CH_3$ | 6-$CH_3$ | Br | 159-161 | $C_{21}H_{27}BrN_2O_2$ |
| 9 | hexyl | 2-$CH_3$ | 6-$CH_3$ | Br | 175-177 | $C_{22}H_{29}BrN_2O_2$ |
| 10 | phenylmethyl | 2-$CH_3$ | 6-$CH_3$ | Br | 173.5-176 | $C_{23}H_{23}BrN_2O_2$ |
| 11 | 2-phenylethyl | 2-$CH_3$ | 6-$CH_3$ | Br | 209-210 | $C_{24}H_{25}BrN_2O_2$ |
| 12 | butyl | 2-$C_2H_5$ | 6-$CH_3$ | Br | 93-94.5 | $C_{21}H_{27}BrN_2O_2$ |
| 13 | 2-phenylethyl | 2-$C_2H_5$ | 6-$CH_3$ | Br | 110-112 | $C_{25}H_{27}BrN_2O_2$ |
| 14 | H | 2-$C_2H_5$ | 6-$C_2H_5$ | Br | 259-261 | $C_{18}H_{21}BrN_2O_2$ |
| 15 | $CH_3$ | 2-$C_2H_5$ | 6-$C_2H_5$ | Br | 162-164 | $C_{19}H_{23}BrN_2O_2$ |
| 16 | propyl | 2-$C_2H_5$ | 6-$C_2H_5$ | Br | 123-125 | $C_{21}H_{27}BrN_2O_2$ |
| 17 | pentyl | 2-$C_2H_5$ | 6-$C_2H_5$ | Br | 140-141.5 | $C_{23}H_{31}BrN_2O_2$ |
| 18 | isoamyl | 2-$C_2H_5$ | 6-$C_2H_5$ | Br | 153.5-154.5 | $C_{23}H_{31}BrN_2O_2$ |
| 19 | hexyl | 2-$C_2H_5$ | 6-$C_2H_5$ | Br | 141-143 | $C_{24}H_{33}BrN_2O_2$ |
| 20 | furylmethyl | 2-$C_2H_5$ | 6-$C_2H_5$ | Br | 155.5-157.5 | $C_{23}H_{25}BrN_2O_2$ |
| 21 | 2-ethoxyethyl | 2-$C_2H_5$ | 6-$C_2H_5$ | Br | 138.5-140 | $C_{22}H_{29}BrN_2O_3$ |
| 22 | 3-methoxypropyl | 2-$C_2H_5$ | 6-$C_2H_5$ | Br | 139-140.5 | $C_{22}H_{29}BrN_2O_3$ |
| 23 | phenylmethyl | 2-$C_2H_5$ | 6-$C_2H_5$ | Br | 174-175 | $C_{25}H_{27}BrN_2O_2$ |
| 24 | 2-phenylethyl | 2-$C_2H_5$ | 6-$C_2H_5$ | Br | 173-175 | $C_{26}H_{29}BrN_2O_2$ |
| 25 | 2-propynyl | 2-$C_2H_5$ | 6-$C_2H_5$ | Br | 211-214 | $C_{21}H_{23}BrN_2O_2$ |
| 26 | butyl | 2-Cl | 6-$CH_3$ | Br | 179-180.5 | $C_{19}H_{22}BrClN_2O_2$ |
| 27 | 2-phenylethyl | 2-Cl | 3-Cl | Br | 208.5-211.5 | $C_{22}H_{19}BrCl_2N_2O_2$ |
| 28 | butyl | 2-Cl | 4-Cl | Br | 195.5-196.5 | $C_{18}H_{19}BrCl_2N_2O_2$ |
| 29 | butyl | 2-Cl | 5-Cl | Br | 183.5-185 | $C_{18}H_{19}BrCl_2N_2O_2$ |
| 30 | butyl | 2-Cl | 6-Cl | Br | 200-201.5 | $C_{18}H_{19}BrCl_2N_2O_2$ |
| 31 | pentyl | 2-$C_2H_5$ | 6-$C_2H_5$ | Cl | 130-132 | $C_{23}H_{31}ClN_2O_2$ |
| 32 | 4-fluorophenylmethyl | 2-Cl | 4-Br | Br | 244.5-246.5 | $C_{21}H_{16}Br_2ClFN_2O_2$ |
| 33 | phenylmethyl | 2-$CH_3$ | 6-Cl | Br | 182-184 | $C_{22}H_{20}BrClN_2O_2$ |
| 34 | butyl | 2-$OCH_3$ | 4-Br | Br | 227-229 | $C_{19}H_{22}Br_2N_2O_3$ |
| 35 | 2-phenylethyl | 2-$OCH_3$ | 4-Br | Br | 261-262 | $C_{23}H_{22}Br_2N_2O_3$ |

TABLE 2

| Example No. | IR $\nu$ value (cm$^{-1}$) Method: KBr | NMR Chemical shift $\delta$ value ($CDCl_3$) | Conc. (ppm) | Evaluation Plants X | Y | Z |
|---|---|---|---|---|---|---|
| 1 | 1607<br>1653 | 1.17(6H, t.), 0.7-2.0(7H, m.),<br>2.65(4H, q.), 2.71(3H, s.),<br>2.83(3H, s.), 4.04(2H, t.),<br>7.07(3H, t.), 10.86(1H, br.). | 20<br>100 | 4<br>5 | 4<br>5 | 4<br>4 |
| 2 | 1607<br>1645 | 1.18(6H, t.), 0.8-2.0(7H, m.),<br>2.62(3H, s.), 2.66(4H, q.),<br>2.85(3H, s.), 4.02(2H, s.),<br>7.07(3H, s.), 10.88(1H, br.). | 20<br>100 | 3 | 4 | 4 |
| 3 | 1600<br>1655 | 0.8-2.0(7H, m.), 2.40(3H, s.),<br>2.75(3H, s.), 2.90(3H, s.),<br>4.06(2H, t.), 7.15-8.0(3H, m.),<br>12.10(1H, br.). | 20<br>100 | 2<br>1 | 2<br>2 | 2<br>3 |
| 4 | 1673 | 0.8-2.0(7H, m.), 2.72(3H, s.),<br>2.88(3H, s.), 3.98(2H, t.),<br>6.87-8.08(4H, m.), 12.48(1H, br.). | 20<br>100 | 1<br>1 | 2<br>1 | 1<br>3 |
| 5 | 1603<br>1667 | 2.60(3H, s.), 2.79(3H, s.),<br>5.33(2H, s.), 7.76-8.33(9H, m.),<br>12.4(1H, br.). | 20<br>100 | 1<br>1 | 4<br>4 | 1<br>1 |
| 6 | 1663 | 2.70(3H, s.), 2.90(3H, s.),<br>2.97(2H, t.), 4.20(2H, t.),<br>6.90-7.35(8H, m.), 12.40(1H, br.). | 20<br>100 | 3<br>4 | 4<br>4 | 2<br>3 |
| 7 | 1613<br>1653<br>1663 | 0.8-2.0(7H, m.), 2.30(6H, s.),<br>2.70(3H, s.), 2.81(3H, s.),<br>4.02(2H, t.), 7.00(3H, s.),<br>10.72(1H, br.). | 20<br>100 | 1<br>4 | 3<br>4 | 4<br>4 |
| 8 | 1610<br>1655 | 0.7-2.0(9H, m.), 2.28(6H, s.),<br>2.70(3H, s.), 2.81(3H, s.),<br>4.03(2H, t.), 7.00(3H, s.),<br>10.78(1H, br.). | 20<br>100 | 1<br>4 | 4<br>4 | 4<br>4 |
| 9 | 1650 | 0.7-2.0(11H, m.), 2.30(6H, s.),<br>2.70(3H, s.), 2.82(3H, s.),<br>3.98(2H, t.), 6.99(3H, s.),<br>10.70(1H, br.). | 20<br>100 | 1<br>3 | 2<br>3 | 3<br>3 |
| 10 | 1603<br>1645 | 2.30(6H, s.), 2.61(3H, s.),<br>2.75(3H, s.), 5.30(2H, s.),<br>6.8-7.4(8H, m.),<br>10.72(1H, br.). | 20<br>100 | 2<br>3 | 4<br>4 | 4<br>4 |
| 11 | 1610<br>1660 | 2.25(6H, s.), 2.68(3H, s.),<br>2.81(3H, s.), 2.93(2H, t.), | 20<br>100 | 4<br>4 | 5<br>5 | 4<br>4 |

TABLE 2-continued

| Example No. | IR ν value (cm⁻¹) Method: KBr | NMR Chemical shift δ value (CDCl₃) | Conc. (ppm) | Evaluation Plants X | Y | Z |
|---|---|---|---|---|---|---|
| | | 4.23(2H, t.), 7.0–7.4(8H, m.), 10.60(1H, br.). | | | | |
| 12 | 1607<br>1653 | 1.19(3H, t.), 0.8–2.0(7H, m.),<br>2.31(3H, s.), 2.61(2H, q.),<br>2.77(3H, s.), 2.89(3H, s),<br>10.94(1H, br.). | 20<br>100 | 1<br>3 | 2<br>3 | 3<br>3 |
| 13 | 1610<br>1655 | 1.19(3H, t.), 2.29(3H, s.),<br>2.67(2H, q.), 2.72(3H, s.),<br>2.88(3H, s.), 2.98(2H, t.),<br>4.29(2H, t.), 7.06–7.40(8H, m.),<br>10.73(1H, br.). | 20<br>100 | 4<br>5 | 4<br>5 | 4<br>4 |
| 14 | 1640 | 1.12(6H, t.), 2.20(3H, s.),<br>2.55(4H, q.), 2.59(3H, s.),<br>7.05(3H, s.), 11.78(1H, br.),<br>12.03(1H, br.). | 20<br>100 | 1<br>1 | 3<br>4 | 4<br>4 |
| 15 | 1613<br>1653 | 1.18(6H, t.), 2.63(4H, q.),<br>2.69(3H, s.), 2.80(3H, s.),<br>3,63(3H, s.), 7.07(3H, s.),<br>10.83(1H, br.). | 20<br>100 | 4<br>4 | 5<br>5 | 4<br>4 |
| 16 | 1610<br>1657 | 1.19(6H, t.), 0.84–2.00(5H, m.),<br>2.67(4H, q.), 2.72(3H, s.),<br>2,84(3H, s.), 3.98(2H, d.),<br>7.08(3H, s.), 10.86(1H, br.). | 20<br>100 | 4<br>5 | 5<br>5 | 4<br>4 |
| 17 | 1610<br>1653 | 1.17(6H, t.), 0.7–2.0(9H, m.),<br>2.65(4H, q.), 2.72(3H, s.),<br>2.84(3H, s.), 4.01(2H, t.),<br>7.07(3H, s.), 10.84(1H, br.). | 20<br>100 | 5<br>5 | 5<br>5 | 4<br>4 |
| 18 | 1610<br>1653 | 1.08(6H, d.), 1.18(6H, t.),<br>0.8–1.9(3H, m.), 2.65(4H, q.),<br>2.73(3H, s.), 2.85(3H, s.),<br>4.05(2H, t.), 7.10(3H, s.),<br>10.84(1H, br.). | 20<br>100 | 4<br>5 | 4<br>4 | 3<br>3 |
| 19 | 1610<br>1650 | 1.19(6H, t.), 0.7–2.0(11H, m.),<br>2.66(4H, q.), 2.73(3H, s.),<br>2.86(3H, s.), 4.03(2H, t.),<br>7.08(3H, s.), 10.87(1H, br.). | 20<br>100 | 4<br>4 | 4<br>4 | 4<br>4 |
| 20 | 1607<br>1643 | 1.17(6H, t.), 2.65(4H, q.),<br>2.79(3H, s.), 2.89(3H, s.),<br>5.02(2H, s.), 6.25(2H, m.),<br>7.07(3H, s.), 7.38(1H, m.),<br>10.87(1H, br.). | 20<br>100 | 4<br>4 | 4<br>4 | 4<br>4 |
| 21 | 1610<br>1643 | 1.15(3H, t.), 1.20(6H, t.),<br>2.66(4H, q.), 2.79(3H, s.),<br>2.86(3H, s.), 3.43(2H, q.),<br>3.64(2H, t.), 4.28(2H, t.),<br>7.10(3H, t.), 10.75(1H, br.). | 20<br>100 | 4<br>4 | 4<br>5 | 4<br>4 |
| 22 | 1610<br>1645 | 1.19(6H, t.), 2.03(2H, m.),<br>2.67(4H, q.), 2.75(3H, s.),<br>2.87(3H, s.), 3.34(3H, s.),<br>3.45(2H, t.), 4.23(2H, t.),<br>7.10(3H, s.), 10.87(1H, br.). | 20<br>100 | 4<br>4 | 4<br>5 | 4<br>4 |
| 23 | 1600<br>1653 | 1.19(6H, t.), 2.62(3H, s.),<br>2.65(4H, q.), 2.78(3H, s.),<br>5.30(2H, s.), 6.8–7.4(8H, m.),<br>10.90(1H, br.). | 20<br>100 | 3<br>4 | 4<br>4 | 4<br>4 |
| 24 | 1605<br>1650 | 1.16(6H, t.), 2.64(4H, q.),<br>2.69(3H, s.), 2.82(3H, s.),<br>2.95(2H, t.), 4.26(2H, t.),<br>7.05–7.40(8H, m.), 10.72(1H, br.). | 20<br>100 | 4<br>4 | 5<br>5 | 4<br>4 |
| 25 | 1610<br>1653 | 1.20(6H, t.), 2.52(1H, d.),<br>2.59(4H, q.), 2.81(3H, s.),<br>2.92(3H, s.), 4.62(2H, d.),<br>7.12(3H, s.), 10.73(1H, br.). | 20<br>100 | 4<br>4 | 5<br>5 | 4<br>4 |
| 26 | 1655 | 0.8–2.0(7H, m.), 2.37(3H, s.),<br>2.74(3H, s.), 2.86(3H, s.),<br>4.03(2H, t.), 6.98–7.40(3H, m.),<br>11.27(1H, br.). | 20<br>100 | 1<br>2 | 2<br>3 | 4<br>4 |
| 27 | 1655 | 2.70(3H, s.), 2.88(3H, s.),<br>3.00(2H, t.), 4.23(2H, t.),<br>7.00–8.34(8H, m.),<br>12.50(1H, br.). | 20<br>100 | 4<br>4 | 4<br>4 | 1<br>1 |
| 28 | 1660 | 0.8–2.0(7H, m.), 2.71(3H, s.),<br>2.85(3H, s.), 4.10(2H, t.),<br>7.10–8.38(3H, m.), 12.58(1H, br.). | 20<br>100 | 1<br>1 | 1<br>3 | 3<br>3 |
| 29 | 1660 | 0.8–2.0(7H, m.), 2.73(3H, s.),<br>2.88(3H, s.), 4.06(2H, t.),<br>6.88–8.45(3H, m.), 12.72(1H, br.). | 20<br>100 | 1<br>2 | 1<br>2 | 3<br>3 |
| 30 | 1600 | 0.8–2.1(7H, m.), 2.72(3H, s.), | 20 | 1 | 2 | 3 |

TABLE 2-continued

| Example No. | IR ν value (cm$^{-1}$) Method: KBr | NMR Chemical shift δ value (CDCl$_3$) | Evaluation Conc. (ppm) | Plants X | Y | Z |
|---|---|---|---|---|---|---|
|  | 1675 | 2.87(3H, s.), 4.05(2H, t.), 6.9–7.1(3H, m.), 12.13(1H, br.). | 100 | 3 | 3 | 3 |
| 31 | 1613 | 1.20(6H, t.), 0.7–2.0(9H, m.), | 20 | 5 | 5 | 4 |
|  | 1647 | 2.64(3H, s.), 2.65(4H, q.), 2.86(3H, s.), 3.97(2H, t.), 7.05(3H, s), 10.80(1H, br.). | 100 | 5 | 5 | 4 |
| 32 | 1600 | *2.62(3H, s.), 2.70(3H, s.), | 20 | 1 | 4 | 1 |
|  | 1660 | 6.43(2H, s.), 7.45–7.90(6H, m.), 8.20(1H, d.), 12.05(1H, br.). | 100 | 1 | 4 | 2 |
| 33 | 1600 | 2.10(3H, s.), 2.68(3H, s.), | 20 | 1 | 4 | 4 |
|  | 1660 | 2.87(3H, s.), 5.30(2H, s.), 6.80–7.50(8H, m.), 11.90(1H, br.). | 100 | 4 | 5 | 4 |
| 34 | 1650 | 0.80–1.90(7H, m.), 2.71(3H, s.), | 20 | 1 | 1 | 3 |
|  |  | 2.83(3H, s.), 3.87(3H, s.), 4.07(2H, t.), 6.90(1H, s.), 7.10(1H, d.), 8.85(1H, d.), 12.00(1H, br.). | 100 | 2 | 2 | 3 |
| 35 | 1653 | 2.67(3H, s.), 2.83(3H, s.), | 20 | 1 | 3 | 1 |
|  |  | 2.90(2H, t.), 3.87(3H, s.), 4.27(2H, t.), 6.90–7.30(7H, m.), 8.50(1H, d.), 12.00(1H, br.). | 100 | 1 | 3 | 1 |

X: *Oryza sativa* L.
Y: *Echinochloa crus-galli* L.
Z: *Raphanus sativus* L.
*Solvent: DMSO-d$_6$

What we claim is:

1. A compound of the formula (I)

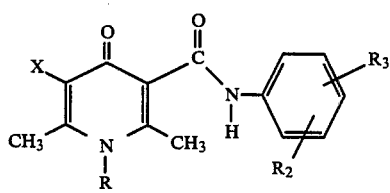

or a salt thereof, wherein R is hydrogen atom or a group of —(CH$_2$)$_n$—R$_1$ in which n is an integer from 1 to 4 and R$_1$ is a hydrogen atom, hydroxy group, lower alkoxy group, mercepto group, lower alkylthio group, amino group, di-lower alkylamino group, C$_{1-11}$ alkyl group, lower alkenyl group, lower alkynyl group, cycloalkyl group, 5- or 6-membered heterocyclic group, wherein said heterocyclic group contains only one to three heteroatoms and wherein said heteroatoms are selected from nitrogen, oxygen, and sulfur, which heterocyclic group may be substituted by lower alkyl, halogen, or a phenyl or naphthyl group that may be substituted by one or two substituents of halogen, lower alkyl, or lower alkoxy; R$_2$ and R$_3$ are substituents on the benzene ring and are, the same or different, a hydrogen atom, halogen atom, cyano group, nitro group, amino group, lower alkyl group, halogenated lower alkyl group, hydroxy group, lower alkoxy group, aryloxy group, carboxy group, or lower alkoxycarbonyl group; and X is a halogen atom.

2. A compound of claim 1 wherein the lower alkyl, lower alkenyl, lower alkynyl or lower alkoxy group in R$_1$, R$_2$ and R$_3$ of the formula (I) has carbon atoms from 1 to 6.

3. A compound of claim 1 wherein the halogen atom in R$_1$, R$_2$ and R$_3$ of the formula (I) is chlorine, bromine or fluorine atom.

4. A compound of claim 1 wherein the heterocyclic group in R$_1$ of the formula (I) is furyl or pyridyl group.

5. A compound of claim 1 wherein

in the formula (I) is 2,6-diethylphenyl, 2-ethyl-6-methylphenyl or 2,6-diisopropylphenyl group.

6. A compound of claim 1 wherein

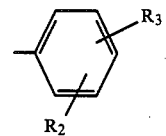

in the formula (I) is 2-methylphenyl, 2-chlorophenyl, 2-chloro-6-methylphenyl, or 2,3-; 2,4-; 2,5- or 2,6-dichlorophenyl group.

7. A compound of claim 1 wherein R in the formula (I) is phenylmethyl, substituted phenylmethyl, 2-phenylethyl, substituted 2-phenylethyl or 3-phenylpropyl group.

8. A compound of claim 1 which is 5-bromo-N-(2,6-diethylphenyl)-1,4-dihydro-2,6-dimethyl-4-oxo-1-phenylmethyl-3-pyridinecarboxamide.

9. A compound of claim 1 which is 5-bromo-N-(2,6-diethylphenyl)-1,4-dihydro-2,6-dimethyl-4-oxo-1-(2-phenylethyl)-3-pyridinecarboxamide.

10. A compound of claim 1 which is 5-bromo-1-butyl-N-(2,6-diethylphenyl)-1,4-dihydro-2,6-dimethyl-4-oxo-3-pyridinecarboxamide.

* * * * *